United States Patent
Neumann

(10) Patent No.: US 6,756,367 B2
(45) Date of Patent: Jun. 29, 2004

(54) BENZO-OXADIAZOLES, -THIADIAZOLES AND -1,4-DIAZINES, PHARMACEUTICAL COMPOSITIONS CONTAINING THEM AND A PROCESS FOR PREPARING THEM

(75) Inventor: Bernhard Peter Neumann, Bern (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/077,150

(22) Filed: Feb. 15, 2002

(65) Prior Publication Data

US 2002/0123629 A1 Sep. 5, 2002

Related U.S. Application Data

(63) Continuation of application No. 09/601,463, filed as application No. PCT/EP99/00622 on Feb. 1, 1999, now abandoned.

(30) Foreign Application Priority Data

Feb. 3, 1998 (GB) ............................................. 9802251

(51) Int. Cl.⁷ ...................... A61K 31/33; A61K 31/505; C07D 239/00; C07D 401/00; C07D 403/00
(52) U.S. Cl. ...................... 514/183; 514/249; 514/256; 544/224; 544/242; 544/235; 544/326; 544/333; 544/336; 544/349; 544/353
(58) Field of Search ................................. 514/183, 249, 514/256; 544/224, 242, 235, 326, 333, 336, 349, 353

(56) References Cited

FOREIGN PATENT DOCUMENTS

| DE | 134184 | 2/1979 |
|---|---|---|
| DE | 3501696 | 7/1986 |
| EP | 405 425 A2 | 1/1991 |
| EP | 0 431 944 A2 | 6/1991 |
| EP | 0 523 533 A1 | 1/1993 |
| EP | 0 602 851 A1 | 6/1994 |
| EP | 0 640 595 A1 | 3/1995 |
| GB | 2 093 450 A | 9/1982 |
| GB | 2 253 846 A | 9/1992 |
| WO | 9220642 * | 11/1992 |
| WO | WO 98/11095 | 3/1998 |

OTHER PUBLICATIONS

Chemical Abstract DN 126: 18845, also cited as Whitten et al(J. Med.Chem.,39/22,4354–57(1996).*
Whitten et al, "Rapid Microscale Synthesis, . . . application to the Synthesis & optimization of CRF receptor antagonists",J.Med. Chem. 39/22,4354–57(1996), also cited as Chemical Abstracts DN 126:18845.*
Joseph T. Coyle et al,"Alzheimer's Disease:A DFisorder of Cortical Cholinergic Innervation",Science,219, 1184–1190(1983).*
Derwent Abstract 93–019579/03.

* cited by examiner

Primary Examiner—Richard L. Raymond
Assistant Examiner—Sudhaker B. Patel
(74) Attorney, Agent, or Firm—Joseph J. Borovian

(57) ABSTRACT

The invention provides a compound of formula I

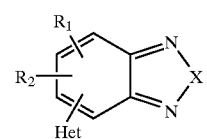

wherein X, $R_1$, $R_2$ and Het are as defined in the description, and a process for preparing them. The compounds of formula I are useful as pharmaceuticals.

6 Claims, No Drawings

BENZO-OXADIAZOLES, -THIADIAZOLES AND -1,4-DIAZINES, PHARMACEUTICAL COMPOSITIONS CONTAINING THEM AND A PROCESS FOR PREPARING THEM

This application is a continuation of U.S. application Ser. No. 09/601,463, filed Oct. 31, 2000, now abandoned, which is a 371 of International Application PCT/EP99/00622, filed Feb. 1, 1999.

The present invention relates to novel benzothiadiazoles and derivatives, their preparation, their use as pharmaceuticals and pharmaceutical compositions containing them.

More particularly the invention provides a compound of formula I

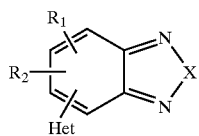

I wherein

X is O, S, N—CH$_3$, CH=CH or CAlk=CAlk, where the Alk independently are (C$_{1-4}$)alkyl, R$_1$ and R$_2$ independently, are hydrogen, halogen, (C$_{1-4}$)alkyl, (C$_{1-4}$)alkoxy or trifluoromethyl, and Het is a radical having one of the formulae (a) to (p) below:

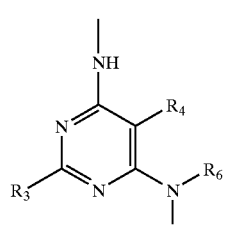

(a)

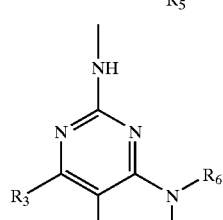

(b)

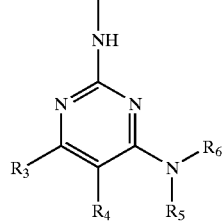

(c)

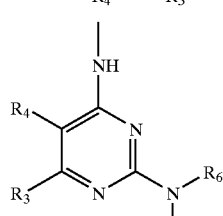

(d)

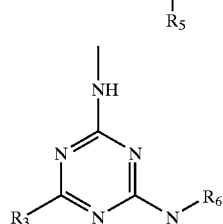

-continued

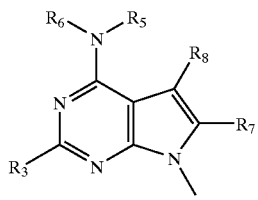

(e)

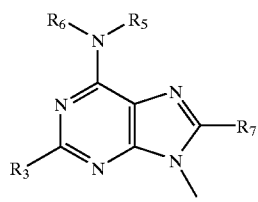

(f)

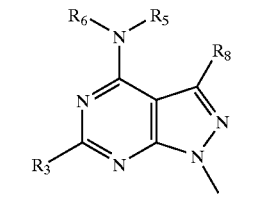

(g)

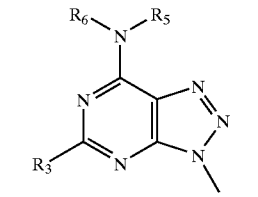

(h)

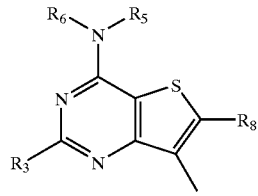

(i)

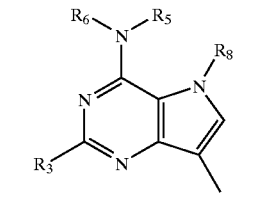

(j)

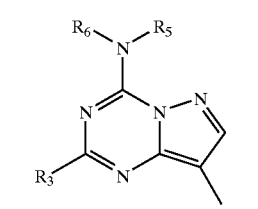

(k)

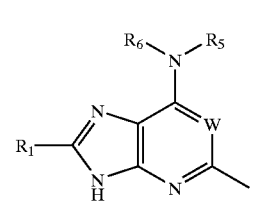

(l)

-continued

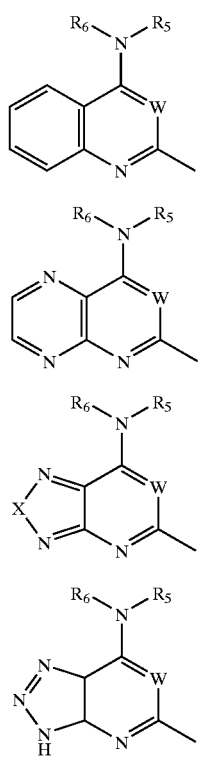

(m)

(n)

(o)

(p)

wherein $R_3$ and $R_8$, independently, are hydrogen or $(C_{1-4})$alkyl, $R_4$ is hydrogen, halogen, $(C_{1-4})$alkyl, cyano, nitro, formyl or $(C_{1-4})$alkylcarbonyl, $R_5$ and $R_6$, independently, are hydrogen, $(C_{1-7})$alkyl, $(C_{3-7})$alkenyl, $(C_{3-7})$cycloalkyl, $(C_{3-7})$cyclo $(C_{1-4})$alkyl, $(C_{1-4})$alkoxy$(C_{2-5})$alkyl or benzyl, $R_7$ is hydrogen, hydroxy, $(C_{1-4})$alkyl or $(C_{1-4})$alkoxy, W is N, C—CN, C—NO$_2$, C—COH or C—CO—Alk where Alk is as defined above, and X is as defined above, in free base or acid addition salt form.

Halogen is fluorine, chlorine, bromine or iodine, preferably fluorine or chlorine.

The radical Het is preferably located on a carbon atom which is adjacent to the heterocyclic moiety in formula I. Preferably Het is of formula (a) to (k), particularly of formula (a).

In a further aspect, the invention provides a process for the production of the compounds of formula I and their salts, whereby a compound of formula II

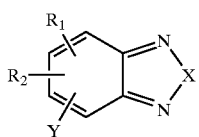

II wherein X, $R_1$ and $R_2$ are as defined above and Y is a radical having one of the formulae (a') to (p') below:

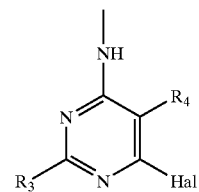

(a')

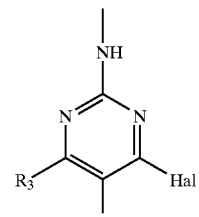

(b')

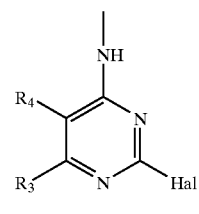

(c')

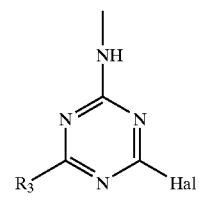

(d')

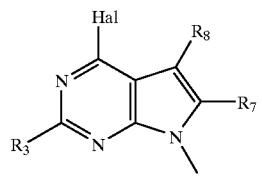

(e')

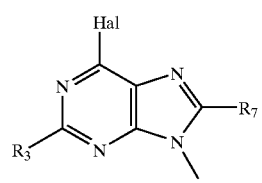

(f')

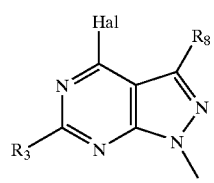

(g')

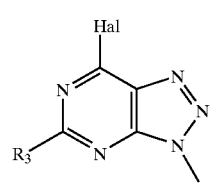

(h')

-continued

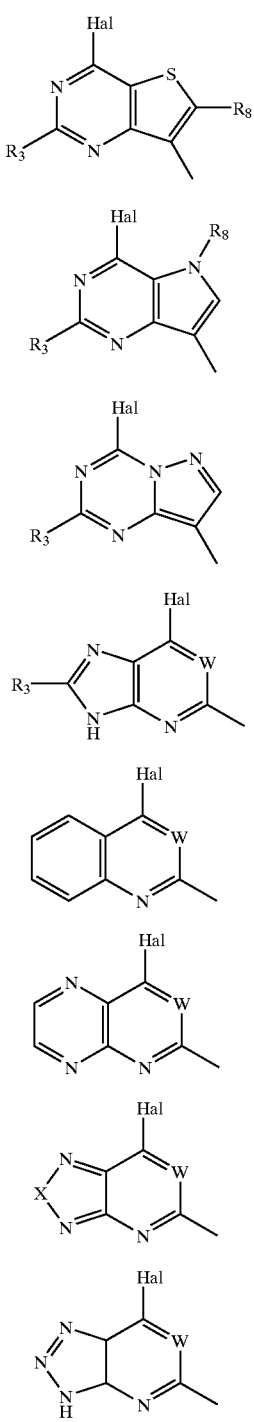

(i')

(j')

(k')

(l')

(m')

(n')

(o')

(p')

wherein $R_3$ to $R_8$, W and X are as defined above and Hal is halogen, is reacted with a compound of formula III

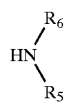

III wherein $R_5$ and $R_6$ are as defined above, and the resulting compound is recovered in free base form or in acid addition salt form.

The reaction may be effected in known manner, e.g. as described in Example 1. Hal is preferably chlorine, bromine or iodine, particularly chlorine.

Working up of the reaction mixtures obtained according to the above process and purification of the compounds thus obtained may be carried out in accordance to known procedures.

Acid addition salts may be produced in known manner from the free base forms and vice-versa. Suitable pharmaceutically acceptable acid addition salts for use in accordance with the present invention include for example the hydrochloride, the hydrogen maleate, the hydrogen fumarate and the hydrogen malonate.

The starting materials of formula II may be obtained as follows:

Compounds of formula II wherein Y is a radical having one of the formulae (a') and (d'), may be obtained by reacting a compound of formula IV

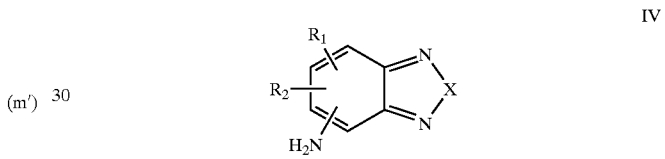

IV wherein X, $R_1$ and $R_2$ are as defined above, with a compound of formula Va or Vd

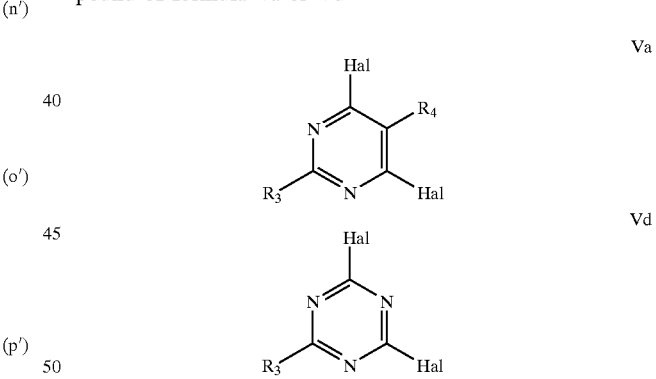

Va

Vd wherein $R_3$ and $R_4$ are as defined above and the Hal independently are halogen.

Compounds of formula II wherein Y is a radical having one of the formulae (b'), (c') and (e') to (l') may be obtained by reaction of POCl$_3$ with a compound of formula VI

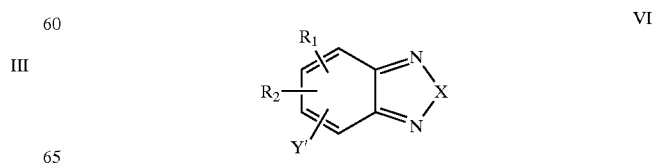

VI wherein Y' is a radical having one of the formulae (b"), (c") and (e") to (l") below

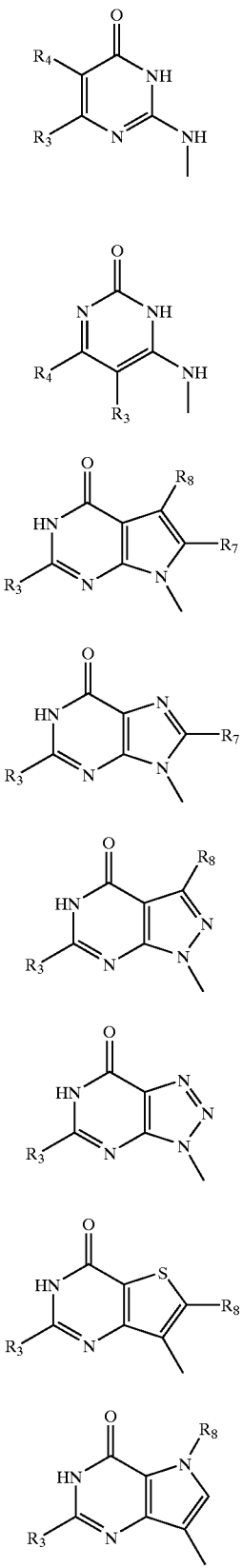

(b")
(c")
(e")
(f")
(g")
(h")
(i")
(j")

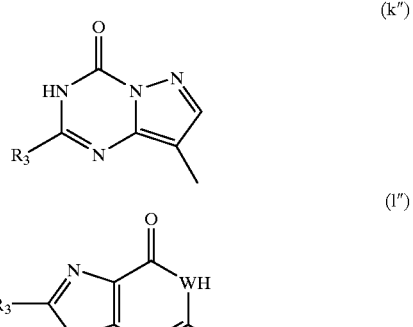

(k")
(l")

wherein $R_3$, $R_4$, $R_7$, $R_8$ and W are as defined above.

All the above mentioned reactions are conventional.

The compounds of formulae III, IV, Va, Vd and VI are know or may be obtained from known compounds, using conventional procedures.

Compounds of formula I and their pharmaceutically acceptable acid addition salts, hereinafter referred to as agents of the invention, exhibit valuable pharmacological properties when tested in vitro using corticotropine releasing factor (CRF) receptor expressing cell cultures, and in animals, and are therefore useful as pharmaceuticals.

In particular the agents of the invention bind to CRF receptors. More particularly they exhibit antagonistic activity at $CRF_1$ receptors, as determined in vitro in the following assay:

Chinese hamster ovary (CHO) cells expressing human recombinant $CRF_1$ (Chen et al., Proc Natl Acad Sci USA 90, 8967–8971, 1993) are propagated in Dulbecco's modified Eagle medium supplemented with 10% foetal calf serum, non-essential aminoacids, 100 U/ml penicillin, 100 mg/l streptomycin and 1 g/l geneticin (G418). For cyclic AMP determinations, cells are grown to confluence in 24-multiwell plates. Stimulation of cyclic AMP accumulation by CRF (human/rat form) is measured in intact cells, using the [$^3$H]adenine labelling technique, as described previously (Schoeffter et al., Neuropharmacology 36, 429–437, 1997). Concentration-response curves for CRF are constructed in the presence of putative antagonists (10 μM) or vehicle (dimethyl sulfoxide 1% vol). $K_B$ values are calculated from the rightward shifts of the control curve, according to the formula: $K_B$=[antagonist, M]/concentration-ratio-1), where the concentration-ratio designates the ratio of CRF $EC_{50}$ value in the presence/CRF $EC_{50}$ value in the absence, of antagonist [Furchgott, In: catecholamines (edited by Blaschko H and Muscholl E) pp. 283–335. Springer, Berlin, 1972].

In this test, the agents of the invention show $CRF_1$ antagonistic activity with Kb $CRF_1$ values of about 1 to 500 nM.

The agents according to the invention are therefore useful in the treatment of any state with increased endogenous level of CRF or in which the HPA (hypothalamic pituitary axis) is disregulated, or of various diseases induced or facilitated by CRF, including inflammatory disorders, such as arthritis, asthma and allergies; anxiety including generalized anxiety; phobic and panic attacks; depression; fatigue syndrome; headache; pain, e.g. inflammatory or neuropathic pain; cancer; irritable bowel syndrome, including Crohn's disease, spastic colon and irritable colon; immune dysfunction; human immunodeficiency virus (HIV) infections; neurodegenerative diseases such as senile dementia, Alzheimer's disease and Parkinson's disease; stroke and head trauma; epilepsy; gastrointestinal diseases; eating and body weight disorders such as obesity and anorexia nervosa; hemorrhagic stress; drug and alcohol withdrawal symptoms; drug addiction; sleeping disorders; hormonal disregulations; skin disorders; stress-induced psychotic episodes; fertility problems; sexual dysfunctions and pre-term birth.

The utility of the agents of the invention in the above indicated diseases could be confirmed in a range of standard tests:

For example the anxiolytic activity of the agents of the invention could be confirmed in the mouse elevated plus-maze [see for example Rodgers R. J., Behavioural Pharmacology 8: 477–496 (1997) where the relevance of the elevated plus-maze is discussed on p. 486; for the method, see Rodgers R. J. et al. Ethology and Psychopharmacology (Eds S J Cooper and C A Hendrie), pp 9–44 (1994), J. Wiley, Chichester]. In this test, the agents of the invention show anxiolytic-like effects on administration of 0.1 to 30 mg/kg p.o.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, In divided doses up to four times a day or in sustained release form.

The agent of the invention may be administered by any conventional route, in particular enterally, preferably orally, for example in the form of tablets or capsules, or parenterally, for example in the form of injectable solutions or suspensions.

For the above-mentioned indications a preferred compound is the compound of Example 1 below. In the above-described binding test said compound exhibits $CRF_1$ antagonistic activity with a Kb $CRF_1$ of 36 nM. In the above-described elevated plus-maze, doses of 0.1 to 10 mg/kg p.o. (with a maximum at 3 mg/kg) significantly affect the anxiety-related behavioural parameters. In contrast to the standard chlordiazepoxide, parameters related to motor stimulation are not affected, which indicates that the observed anxiolytic effects are not attributable to a general motor stimulation.

In accordance with the foregoing, the present invention also provides an agent of the invention, for use as a pharmaceutical, e.g. for the treatment of diseases induced or facilitated by CRF, such as these indicated above.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

Moreover the present invention provides the use of an agent of the invention, for the manufacture of a medicament for the treatment of any condition mentioned above.

In still a further aspect the present invention provides a method for the treatment of any condition mentioned above, in a subject in need of such treatment, which comprises administering to such subject a therapeutically effective amount of an agent of the invention.

The following examples illustrate the invention. The temperatures are given in degrees Celsius and are uncorrected.

EXAMPLE 1

5,7-dimethyl-4-[2,5-dimethyl-6-(di-n-propyl)-amino-pyrimidin-4-yl]-amino-2,1,3-benzothiadiazole A solution of 4-(4-chloro-2,5-dimethyl-pyrimidin-6-yl)-amino-5,7-dimethyl-2,1,3-benzothiadiazole (3.5 g) and di-n-propylamine (5.35 ml) in abs. n-methylpyrrolidone (35 ml) is stirred at 157° in a sealed vessel for 96 hours. The reaction is monitored using thin layer chromatography. The reaction mixture is cooled, 50 ml water are added and the aqueous phase is extracted twice with methyl-t-butylether (2×200 ml). The organic phase is dried, evaporated and chromatographically separated on silicagel using cyclohexane/methyl-t-butylethan (5:1). The appropriate fraction is evaporated and the residue recrystallised from methanol to give the title product. Mp=117–119°.

The starting material 4-(4-chloro-2,5-dimethyl-pyrimidin-6-yl)-amino-5,7-dimethyl-2,1,3-benzothiadiazole is produced as follows:

4,6-Dimethyl-2,1,3-benzothiadiazole (7.7 g) is disolved in conc. sulphuric acid (20 ml), cooled under stirring to 0–5° and nitric acid (2.5 ml; d=1.52) is added dropwise. The clear solution is poured on ice, the so obtained precipitate is filtered off and washed with water. The resulting 5,7-dimethyl-4-nitro-2,1,3-benzothiadiazole is recrystallized from cyclohexane. Mp=105–106°.

5,7-Dimethyl-4-nitro-2,1,3-benzothiadiazole (20 g) is warmed to ebullition in water (2.2 l) and ethanol (2.2 l) and sodium dithionite is added portionwise (strongly exothermic reaction). The reaction mixture is immediately cooled in an ice bath and extracted with ethyl acetate. The organic phase is concentrated by evaporation and the residue recrystallised in water to give 4-amino-5,7-dimethyl-2,1,3-benzothiadiazole. Mp=113–114°.

4-Amino-5,7-dimethyl-2,1,3-benzothiadiazole (4 g) is added in portions to a 55%-dispersion of sodium hydride (2.72 g) in abs. tetrahydrofuran (50 ml) under an argon atmosphere. The mixture is stirred at 25–30 for 3 hours, then a solution of 4,6-dichloro-2,5-dimethyl-pyrimidine (4 g) in abs. tetrahydrofuran (20 ml) is added in drops at 5° during 30 minutes. The reaction mixture is stirred at room temperature for 16 further hours, then ice water is carefully added. The resulting precipitate is washed with water and a few ml of methanol. After recrystallisatlon from methanol or cyclohexane, 4-(4-chloro-2,5-dimethyl-pyrimidin-6yl)-amino-5,7-dimethyl-2,1,3-benzothiadiazole is obtained. Mp=174–177°.

The following compounds of formula I are prepared analogously to example 1:
a) Compounds of Formula

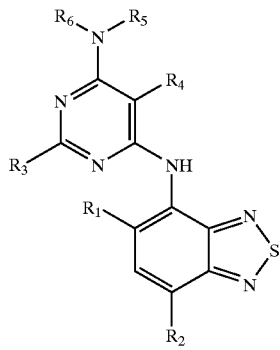

| Ex. | $R_1$ | $R_2$ | $R_3$ | $R_4$ | $R_5$ | $R_6$ | Mp |
|---|---|---|---|---|---|---|---|
| 2 | Me | Me | Me | Me | n-Propyl | —CH$_2$-Cyclopropyl | 120–121° |
| 3 | Me | Me | Me | H | n-Propyl | —CH$_2$-Cyclopropyl | 124–127° * |
| 4 | Me | Me | Me | H | n-Propyl | n-Propyl | 177–179° * |
| 5 | Me | Me | Me | Cl | n-Propyl | n-Propyl | 106–108° |
| 6 | Me | Me | Me | Cl | n-Propyl | —CH$_2$-Cyclopropyl | 111–113° |
| 7 | Me | Me | Me | Me | n-Propyl | Et | 101–102° |
| 8 | Me | Me | Me | Me | n-Butyl | Et | 83–84° |
| 9 | Me | Me | Me | Me | —CH$_2$CH$_2$OCH$_3$ | —CH$_2$CH$_2$OCH$_3$ | 70–73° |
| 10 | Me | Me | Me | Me | —CH$_2$—CH(CH$_3$)—CH$_3$ | —CH$_2$—CH(CH$_3$)—CH$_3$ | 104–105° |
| 11 | Me | Me | Me | Me | 3-Pentyl | H | 113–115° |
| 12 | Me | Me | Me | Me | 2-Butyl | H | 88° |
| 13 | Me | Me | Me | CN | n-Propyl | n-Propyl | 171–173° |
| 14 | Me | Me | Me | CN | n-Propyl | —CH$_2$-Cyclopropyl | 165–167° |
| 15 | Cl | Cl | Me | Me | Me | Et | 116° |
| 16 | Cl | Cl | Me | Me | Me | n-Butyl | 105° |
| 17 | Cl | Cl | Me | Me | Et | Et | 189–193° * |
| 18 | Cl | Cl | Me | Me | Et | n-Propyl | 107° |
| 19 | Cl | Cl | Me | Me | Et | n-Butyl | 101° |
| 20 | Cl | Cl | Me | Me | n-Propyl | n-Propyl | 118–121° |
| 21 | Cl | Cl | Me | Me | n-Propyl | —CH$_2$-Cyclopropyl | 120–123° |
| 22 | Cl | Cl | Me | Me | n-Butyl | n-Butyl | 56° |
| 23 | Cl | Cl | Me | Me | Allyl | Allyl | 112° |
| 24 | Cl | Cl | Me | Me | H | Benzyl | 126° |
| 25 | Cl | Cl | Me | Me | Me | Benzyl | 138° |
| 26 | Me | Cl | Me | Me | n-Propyl | n-Propyl | 102–104° |
| 27 | Me | Cl | Me | Me | n-Propyl | —CH$_2$-Cyclopropyl | 131–132° |
| 28 | Cl | Me | Me | Me | n-Propyl | —CH$_2$-Cyclopropyl | 110–112° |
| 29 | Cl | Me | Me | Me | n-Propyl | n-Propyl | 112–114° |
| 30 | Cl | H | Me | Me | n-Propyl | n-Propyl | 77–80° |
| 31 | Me | H | Me | Me | n-Propyl | n-Propyl | 95–98° |

Me = Methyl;
Et = ethyl;
* Fumarate b) Compounds of Formula

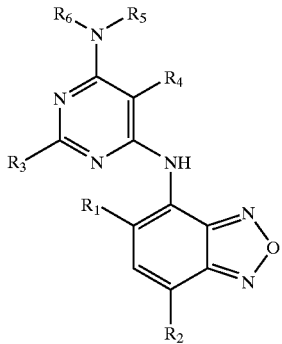

| Ex. | $R_1$ | $R_2$ | $R_3$ | $R_4$ | $R_5$ | $R_6$ | Mp |
|---|---|---|---|---|---|---|---|
| 32 | Me | Me | Me | Me | n-Propyl | n-Propyl | 123° |
| 33 | Cl | Me | Me | Me | n-Propyl | n-Propyl | 100° |
| 34 | Me | Me | Me | Me | n-Propyl | —CH$_2$-Cyclopropyl | 105° |
| 35 | Cl | Me | Me | Me | n-Propyl | —CH$_2$-Cyclopropyl | 86° |
| 36 | Me | Me | Me | Me | n-Propyl | Et | 102° |
| 37 | Me | Me | Me | Me | n-Butyl | Et | 71° |

Me = Methyl;
Et = Ethyl c) Compounds of Formula

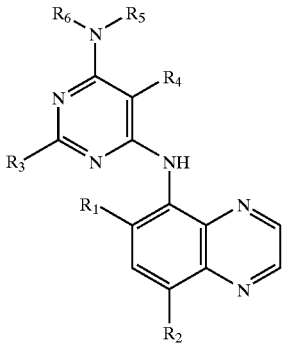

| Ex. | $R_1$ | $R_2$ | $R_3$ | $R_4$ | $R_5$ | $R_6$ | Mp |
|---|---|---|---|---|---|---|---|
| 38 | Me | Me | Me | Me | n-Propyl | n-Propyl | 94–96° |
| 39 | Cl | Cl | Me | Me | n-Propyl | n-Propyl | 126–128° |
| 40 | Cl | Me | Me | Me | n-Propyl | n-Propyl | 107–109° |
| 41 | Cl | Me | Me | Me | n-Propyl | —CH$_2$-Cyclopropyl | 115–117° |
| 42 | Me | Me | Me | Me | n-Propyl | —CH$_2$-Cyclopropyl | 105–106° |
| 43 | Cl | Cl | Me | Me | n-Propyl | —CH$_2$-Cyclopropyl | 126–127° |
| 44 | Cl | Cl | Me | Me | Et | n-Propyl | 120–123° |
| 45 | Me | Me | Me | Me | Et | n-Propyl | 109–110° |
| 46 | Cl | Me | Me | Me | Et | n-Butyl | 117–119° |
| 47 | Me | Me | Me | Me | Et | n-Butyl | 106–107° |

Me = Methyl;
Et = Ethyl d) Compounds of Formula

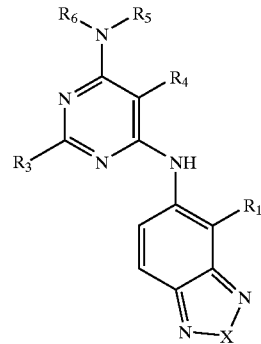

| Ex. | X | $R_1$ | $R_3$ | $R_4$ | $R_5$ | $R_6$ | Mp |
|---|---|---|---|---|---|---|---|
| 48 | S | Cl | Me | Me | Et | n-Butyl | 85° |
| 49 | S | Cl | Me | Me | n-Propyl | —CH$_2$-Cyclopropyl | 84° |
| 50 | CH=CH | Br | Me | Me | Et | n-Butyl | 110° |
| 51 | CH=CH | Br | Me | Me | n-Propyl | —CH$_2$-Cyclopropyl | 135° |

Me = Methyl;
Et = Ethyl e) Compounds of Formula

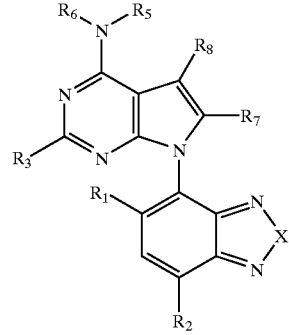

| Ex. | X | $R_1$ | $R_2$ | $R_3$ | $R_5$ | $R_6$ | $R_7$ | $R_8$ | Mp |
|---|---|---|---|---|---|---|---|---|---|
| 52 | S | Me | Me | Me | Et | n-Butyl | Me | Me | 90–92° |
| 53 | CH=CH | Me | Me | Me | Et | n-Butyl | Me | Me | 106–108° |
| 54 | S | Me | Me | Me | n-Propyl | n-Propyl | Me | Me | 126–128° |
| 55 | CH=CH | Me | Me | Me | n-Propyl | n-Propyl | Me | Me | 156–158° |
| 56 | S | Cl | Me | Me | n-Propyl | n-Propyl | Me | Me | 135–136° |
| 57 | CH=CH | Cl | Me | Me | n-Propyl | n-Propyl | Me | Me | 130–131° |
| 58 | S | Cl | Me | Me | Et | n-Butyl | Me | Me | 90–92° |
| 59 | CH=CH | Cl | Me | Me | Et | n-Butyl | Me | Me | 177–178° |

Me = Methyl;
Et = Ethyl f) The compound of Formula

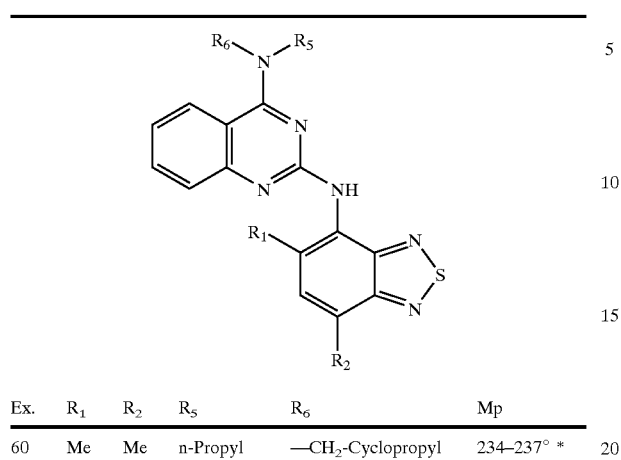

| Ex. | $R_1$ | $R_2$ | $R_5$ | $R_6$ | Mp |
|---|---|---|---|---|---|
| 60 | Me | Me | n-Propyl | —CH$_2$-Cyclopropyl | 234–237° * |

Me = Methyl;
* Fumarate

What is claimed is:

1. A compound of formula I

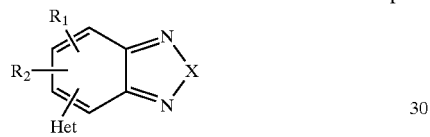

wherein

X is O, S, N—CH$_3$, CH=CH or CAlk=CAlk, where the Alk independently are (C$_{1-4}$)alkyl, $R_1$ and $R_2$ independently, are hydrogen, halogen, (C$_{1-4}$)alkyl, (C$_{1-4}$)alkoxy or trifluoromethyl, and Het is a radical having one of the formulae (a) to (p) below:

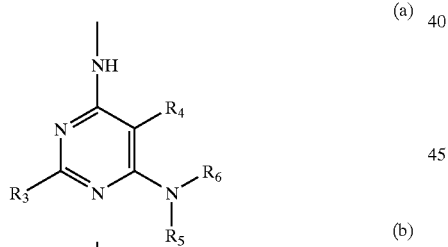
(a)

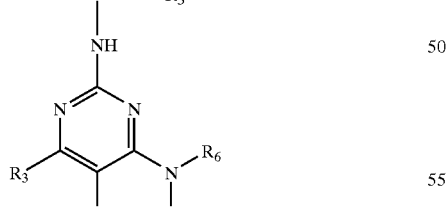
(b)

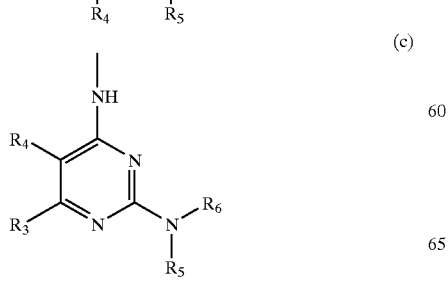
(c)

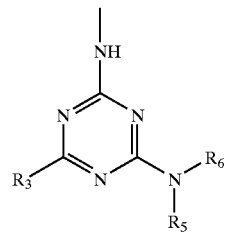
(d)

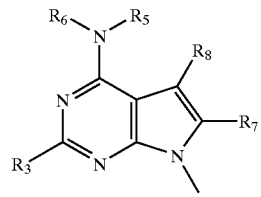
(e)

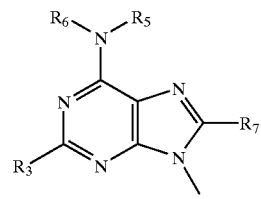
(f)

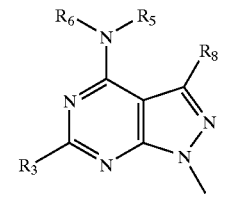
(g)

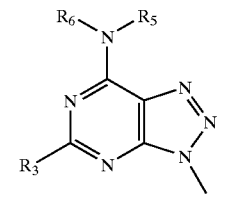
(h)

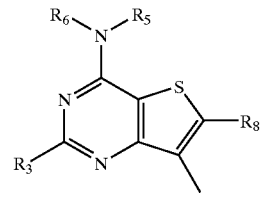
(i)

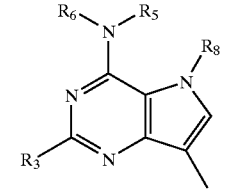
(j)

-continued (k)
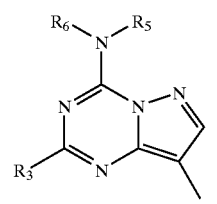

(l)
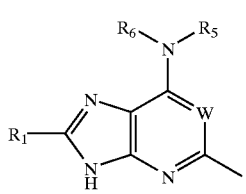

(m)
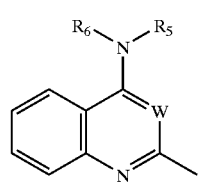

(n)
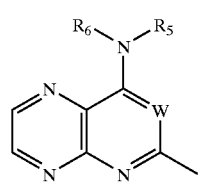

(o)
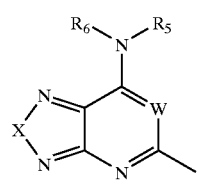

(p)
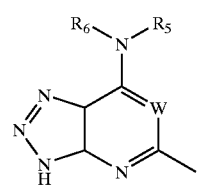

wherein
$R_3$ and $R_8$, independently, are hydrogen or $(C_{1-4})$alkyl,
$R_4$ is hydrogen, $(C_{1-4})$alkyl, cyano, nitro, formyl or $(C_{1-4})$alkylcarbonyl,
$R_5$ and $R_6$, independently, are hydrogen, $(C_{1-7})$alkyl, $(C_{3-7})$alkenyl, $(C_{3-7})$cycloalkyl, $(C_{3-7})$cycloalky$(C_{1-4})$alkyl, $(C_{1-4})$alkoxy$(C_{2-5})$alkyl or benzyl,
$R_7$ is hydrogen, hydroxy, $(C_{1-4})$alkyl or $(C_{1-4})$alkoxy,
W is N, C—CN, C—NO$_2$, C—COH or C—CO—Alk where Alk is as defined above, and
X is as defined above,
in free base or acid addition salt form.

2. 5,7-Dimethyl4-[2,5-dimethyl-6-(di-n-propyl)-anino-pyrimidin4-yl]amino-2,1, 3-benzothiadiazole in free base or acid addition salt form.

3. A process for the preparation of a compound of formula I as defined in claim 1, or a salt thereof, which includes the step of reacting a compound of formula II II
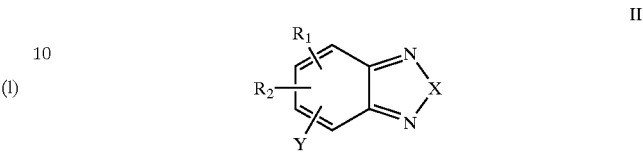

wherein X, $R_1$ and $R_2$ are as defined in claim 1 and Y is a radical having one of the formulae (a') to (p') below:

(a')
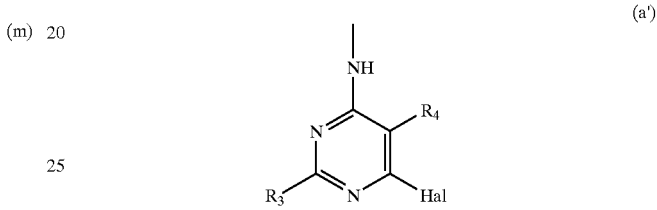

(b')
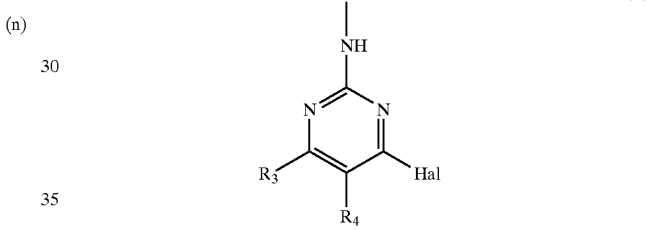

(c')
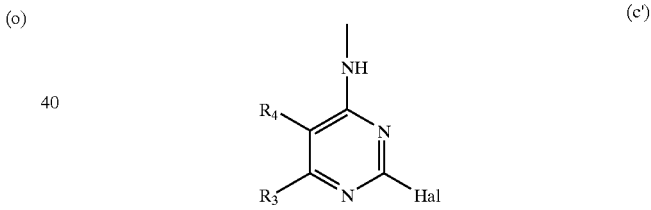

(d')
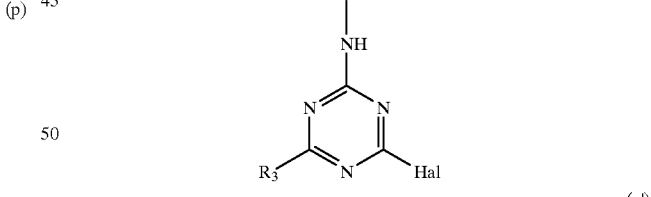

(e')
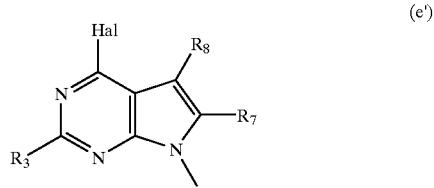

(f')
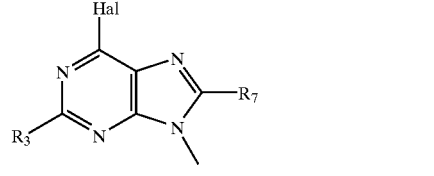

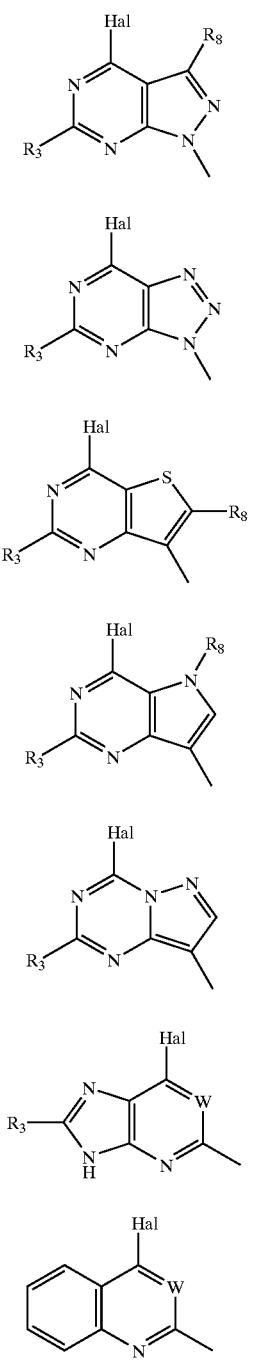

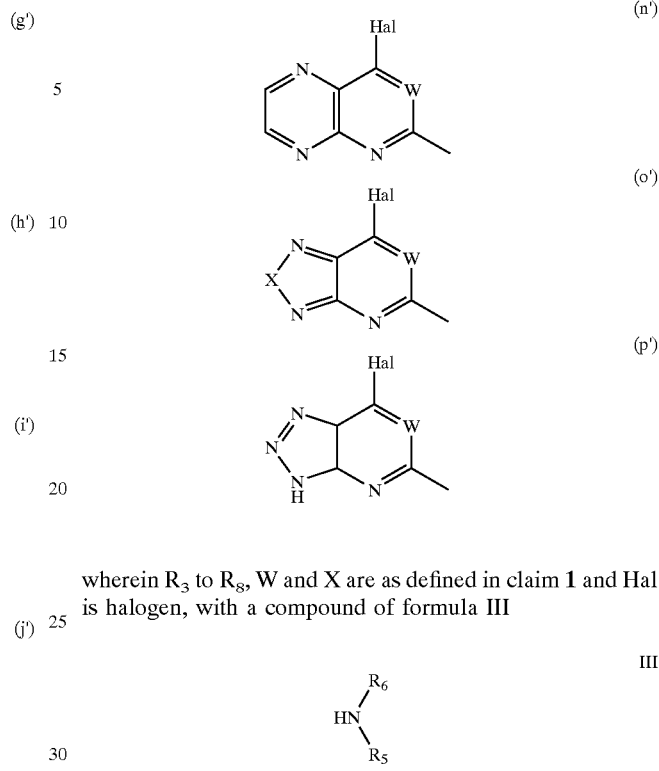

wherein $R_3$ to $R_8$, W and X are as defined in claim 1 and Hal is halogen, with a compound of formula III $$III$$

wherein $R_5$ and $R_6$ are as defined in claim 1, and recovering the thus obtained compound of formula I in free base or acid addition salt form.

4. A compound of claim 1 which is N-(6-chloro-8-methyl-quinoxalin-5-yl)-N'-cyclopropylmethyl-2,5-dimethyl-N'-n-propyl-pyrimidine-4,6-diamine, in free base or acid addition salt form.

5. A pharmaceutical composition comprising a pharmaceutically acceptable carrier and a therapeutically effective amount of a compound of claim 1, in free base or pharmaceutically acceptable acid addition salt form.

6. A method of treating diseases which are responsive to the antagonism of $CRF_1$ receptors comprising administering to a subject in need of such treatment a therapeutically effective amount of a compound of claim 1, in free base or pharmaceutically acceptable acid addition salt form.

* * * * *